(12) United States Patent
Di Girolamo et al.

(10) Patent No.: US 8,134,043 B2
(45) Date of Patent: Mar. 13, 2012

(54) ABSORBENT ARTICLES WITH IMPROVED ACQUISITION RATE

(75) Inventors: Remo Di Girolamo, Pescara (IT); Ivana Spinelli, Pescara (IT); Fabrizio Tinghino, Montesilvano (IT)

(73) Assignee: The Procter and Gamble Company, Cincinnati, OH (US)

( * ) Notice: Subject to any disclaimer, the term of this patent is extended or adjusted under 35 U.S.C. 154(b) by 463 days.

(21) Appl. No.: 11/216,499

(22) Filed: Aug. 31, 2005

(65) Prior Publication Data

US 2006/0058750 A1 Mar. 16, 2006

(30) Foreign Application Priority Data

Sep. 13, 2004 (EP) .................................. 04021673

(51) Int. Cl.
*A61F 13/15* (2006.01)
*A61F 13/20* (2006.01)
(52) U.S. Cl. ......... 604/380; 604/379; 604/378; 604/358
(58) Field of Classification Search .................. 604/378, 604/379, 380, 385.01, 383
See application file for complete search history.

(56) References Cited

U.S. PATENT DOCUMENTS

| 3,364,931 | A |  | 1/1968 | Hirsch |  |
|---|---|---|---|---|---|
| 3,929,135 | A |  | 12/1975 | Thompson |  |
| 4,029,101 | A |  | 6/1977 | Chesky |  |
| 4,430,148 | A |  | 2/1984 | Schaefer |  |
| 4,501,586 | A |  | 2/1985 | Holtman |  |
| 4,515,595 | A |  | 5/1985 | Kievit |  |
| 4,531,999 | A |  | 7/1985 | Persson |  |
| 4,624,666 | A | * | 11/1986 | DeRossett et al. | ............ 604/366 |
| 4,710,189 | A |  | 12/1987 | Lash |  |
| 4,762,521 | A | * | 8/1988 | Roessler et al. | ......... 604/385.26 |
| 4,777,073 | A |  | 10/1988 | Sheth |  |
| 4,808,252 | A |  | 2/1989 | Lash |  |
| 4,823,783 | A |  | 4/1989 | Willhite |  |
| 4,834,735 | A |  | 5/1989 | Alemany |  |

(Continued)

FOREIGN PATENT DOCUMENTS

CA 2306605 10/2000

(Continued)

OTHER PUBLICATIONS

PCT International Search Report dated Feb. 16, 2006.

*Primary Examiner* — Tatyana Zalukaeva
*Assistant Examiner* — Susan Su
(74) *Attorney, Agent, or Firm* — Andres E. Velarde; Amanda T. Barry; Gary Foose

(57) ABSTRACT

A disposable absorbent product (20) such as, e.g. a baby diaper, an adult incontinence pad, a sanitary napkin or the like, includes a liquid pervious topsheet (24), a liquid impervious backsheet (26), and an absorbent core (28) positioned between the topsheet (24) and the backsheet (26). The absorbent core (28) has a liquid receiving surface directed towards said topsheet (24), and the absorbent core (28) is provided with at least one embossing (50) forming a channel for liquid drainage at said receiving surface. Preferably an acquisition layer (40) is provided between the topsheet (24) and the absorbent core (28). The acquisition layer preferably extends into the embossing (50), while a resilient absorbent member (30) is preferably provided between the absorbent core (28) and the acquisition layer (40) in the form of stripes arranged longitudinally spaced along the upper longitudinal sides of the channel (50) formed by the embossing.

1 Claim, 2 Drawing Sheets

U.S. PATENT DOCUMENTS

| | | |
|---|---|---|
| 4,854,984 A | 8/1989 | Ball |
| 4,919,756 A | 4/1990 | Sawdai |
| 4,950,264 A | 8/1990 | Osborn, III |
| 5,009,653 A | 4/1991 | Osborn, III |
| 5,030,229 A | 7/1991 | Yang |
| 5,047,023 A | 9/1991 | Berg |
| 5,102,597 A | 4/1992 | Roe |
| 5,124,188 A | 6/1992 | Roe |
| 5,149,344 A | 9/1992 | Macy |
| 5,234,422 A | 8/1993 | Sneller |
| 5,260,345 A | 11/1993 | DesMarais |
| 5,268,224 A | 12/1993 | DesMarais |
| 5,331,015 A | 7/1994 | DesMarais |
| 5,423,788 A * | 6/1995 | Rollins et al. ............ 604/385.21 |
| 5,460,623 A | 10/1995 | Emenaker |
| 5,549,589 A | 8/1996 | Horney |
| 5,827,254 A | 10/1998 | Trombetta |
| 5,830,202 A * | 11/1998 | Bogdanski et al. ........... 604/378 |
| 5,925,026 A | 7/1999 | Myers et al. |
| 6,241,714 B1 | 6/2001 | Aschenbrenner et al. |
| 6,528,439 B1 * | 3/2003 | Stokes et al. ................ 442/352 |
| 6,573,424 B1 | 6/2003 | Aschenbrenner et al. |
| 7,686,790 B2 * | 3/2010 | Rasmussen et al. ......... 604/317 |
| 2002/0040212 A1 | 4/2002 | Drevik |
| 2002/0052587 A1 | 5/2002 | Magnusson et al. |
| 2007/0073256 A1 * | 3/2007 | Ponomarenko et al. . 604/385.13 |

FOREIGN PATENT DOCUMENTS

| | | |
|---|---|---|
| EP | 0 512 010 B1 | 11/1992 |
| WO | WO 93/11725 A1 | 6/1993 |
| WO | WO 95/07674 A2 | 3/1995 |
| WO | WO 9824960 A1 * | 6/1998 |
| WO | WO 01/21873 | 3/2001 |

* cited by examiner

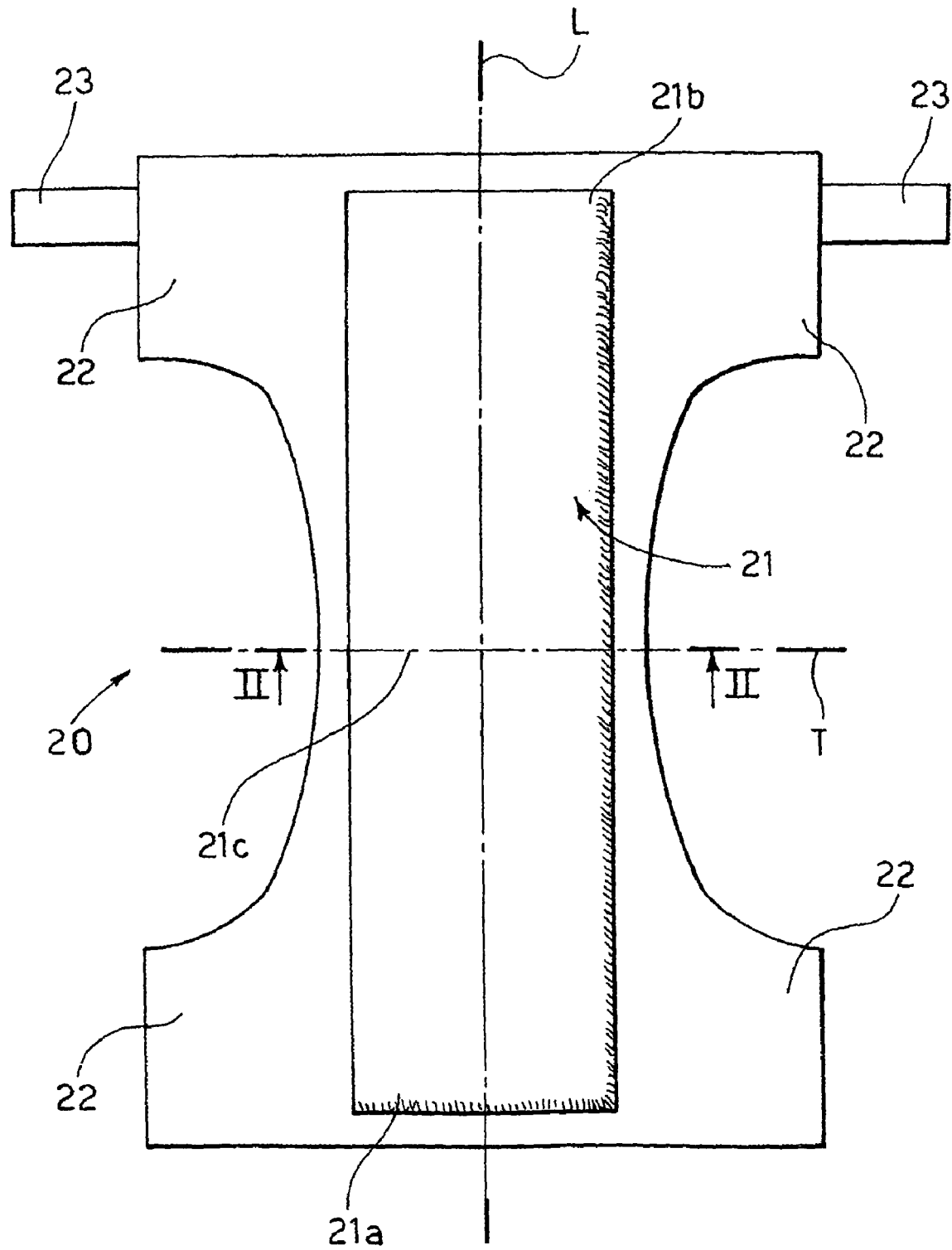

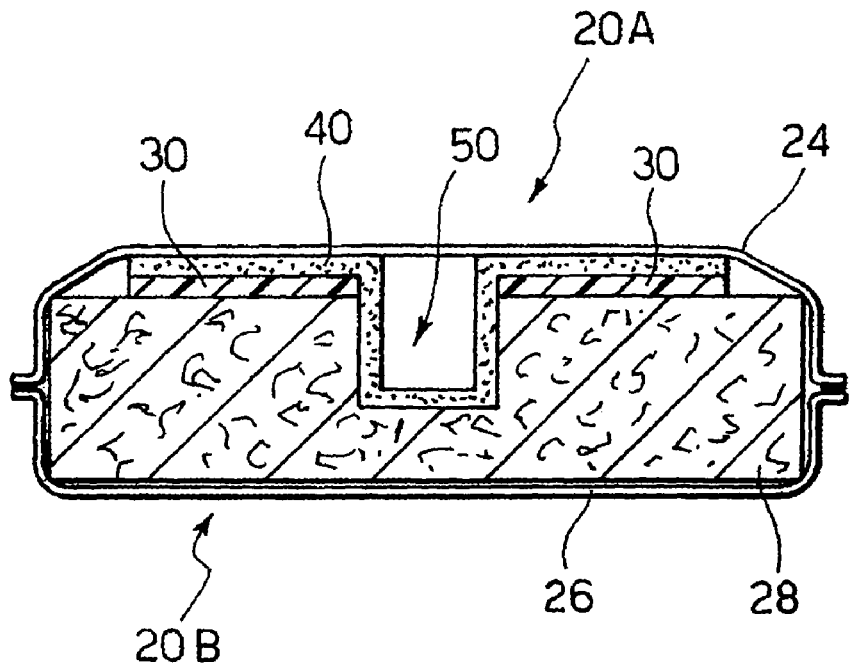
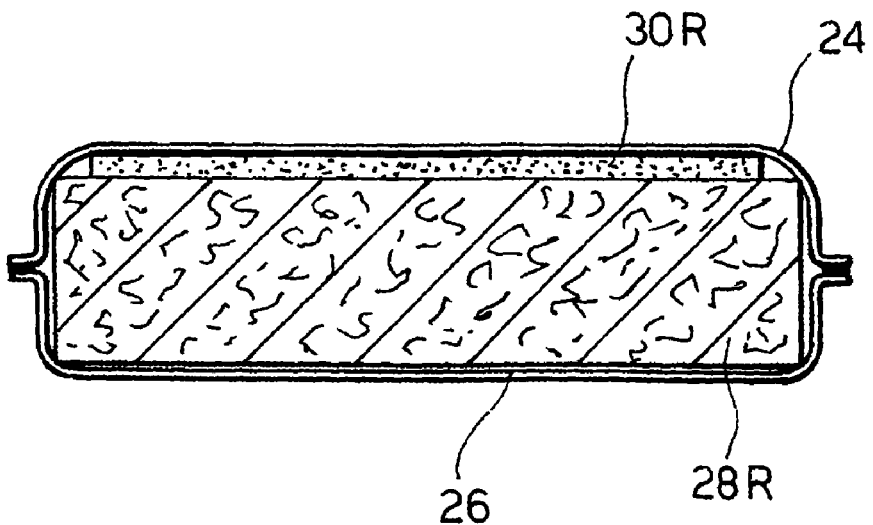

ABSORBENT ARTICLES WITH IMPROVED ACQUISITION RATE

FIELD OF THE INVENTION

The present invention relates to disposable absorbent articles (oftentimes referred to as absorbent aids) such as diapers, adult incontinence pads, sanitary napkins, and the like.

DESCRIPTION OF THE RELATED ART

A key requirement for absorbent aids is protection. Protection is essentially related to three basic factors, namely:
  i) absorption capacity (linked to absorbent core Specific Absorbent Capacity or SAC, typically measured as grams of liquid absorbed per gram of absorbent core—g/g),
  ii) leakage protection (linked to acquisition speed, typically measured as milliliters of liquid absorbed per time unit—ml/sec, and diffusion—measured as mm), and
  iii) dryness (typically measured as rewetting—i.e. grams of liquid leaving the absorbent core under specified conditions).

Methods to increase absorption capacity include increasing the amount of absorbent materials (e.g., cellulose) and/or incorporating superabsorbent substances such as absorbent gelling materials to the fibrous absorbent material. EP Pat. 0512010 B1 is exemplary of absorbent structures using cellulosic fibers and superabsorbent material.

Absorbent gelling materials are especially useful in enhancing absorption capacity and particularly the specific absorption capacity. Water-insoluble, water-swellable, hydrogel-forming absorbent polymers are capable of absorbing large quantities of liquids such as body fluids (e.g., urine, blood, menstrual fluid) and are further capable of retaining such absorbed liquids under moderate pressures. These absorption characteristics of such polymer materials make them especially useful for incorporation into absorbent articles such as disposable diapers, adult incontinence pads and briefs, and catamenial products such as sanitary napkins, and the like.

The development of highly absorbent members used in such absorbent articles are the subject of substantial commercial interest.

In this regard, the use of certain absorbent polymers often referred to as "hydrogels" "superabsorbents" or "hydrocolloid" material, has been particularly important.

Absorbent gelling materials are also suitable to improve dryness, since these materials have high retention capacity under pressure. However, the amount of superabsorbent materials that can be incorporated to an absorbent article is limited by a number of factors.

For instance, the permeability or flow conductivity of the gel layer formed by swelling in the presence of body fluids is extremely important when these absorbent polymers are used in absorbent cores or members at a high concentration in localized or throughout regions thereof. It should be noted that lack of liquid permeability or flow conductivity of absorbent polymers may directly impact on the ability of resultant gel layers to acquire and distribute body fluids.

Absorbent gelling materials may in fact be affected by "gel blocking". That has strong negative impact on the effectiveness of the absorbing aids in acquiring/diffusing the liquid. "Gel blocking" occurs when particles of the hydrogel-forming absorbent polymer are wetted and the particles swell so as to inhibit fluid transmission to other regions of the absorbent structure. Wetting of these other regions of the absorbent member therefore takes place via a very slow diffusion process. In practical terms, this means that acquisition of fluids by the absorbent structure is much slower than the rate at which fluids are discharged, especially in gush situations.

Leakage from the absorbent article can take place well before the particles of hydrogel-forming absorbent polymer in the absorbent member are fully saturated or before the fluid can diffuse or wick past the "blocking" particles into the rest of the absorbent member. Gel blocking can be a particularly acute problem if the particles of hydrogel-forming absorbent polymer do not have adequate gel strength and deform or spread under stress once the particles swell with absorbed fluid.

This gel blocking phenomenon has typically necessitated the use of a fibrous matrix in which are dispersed the particles of hydrogel-forming absorbent polymer. This fibrous matrix keeps the particles of hydrogel-forming absorbent polymer separated from one another. This fibrous matrix also provides a capillary structure that allows fluid to reach the hydrogel-forming absorbent polymer located in regions remote from the initial fluid discharge point. See U.S. Pat. No. 4,834,735.

However, dispersing the hydrogel-forming absorbent polymer in a fibrous matrix at relatively low concentrations in order to minimize or avoid gel blocking can lower the overall fluid storage capacity of thinner absorbent structures. Using lower concentrations of these hydrogel-forming absorbent polymers limits somewhat the real advantage of these materials, namely their ability to absorb and retain large quantities of body fluids per given volume.

Besides increasing gel strength, other physical and chemical characteristics of these hydrogel-forming absorbent polymers have been manipulated to decrease gel blocking. One characteristic is the particle size, and especially the particle size distribution, of the hydrogel-forming absorbent polymer used in the fibrous matrix. For example, particles of hydrogel-forming absorbent polymer having a particle size distribution such that the particles have a mass median particle size greater than or equal to about 400 microns have been mixed with hydrophilic fibrous materials to minimize gel blocking and to help maintain an open capillary structure within the absorbent structure so as to enhance planar transport of fluids away from the area of initial discharge to the rest of the absorbent structure. In addition, the particle size distribution of the hydrogel-forming absorbent polymer can be controlled to improve absorbent capacity and efficiency of the particles employed in the absorbent structure. See U.S. Pat. No. 5,047,023.

However, even adjusting the particle size distribution does not, by itself, lead to absorbent structures that can have relatively high concentrations of these hydrogel-forming absorbent polymers.

Another characteristic that has been looked at in order to minimize gel blocking is to improve the capillary capability of these hydrogel-forming absorbent polymers. In particular, it has been suggested that particles of these hydrogel-forming absorbent polymers be formed into interparticle crosslinked aggregate macrostructures, typically in the form of sheets or strips. See U.S. Pat. Nos. 5,102,597; 5,124,188; and 5,149,344.

Because the particulate nature of the absorbent polymer is retained, these macrostructures provide pores between adjacent particles that are interconnected such that the macrostructure is fluid permeable (i.e., has capillary transport channels). Due to the interparticle crosslink bonds formed between the particles, the resultant macrostructures also have improved structural integrity, increased fluid acquisition and distribution rates, and minimal gel blocking.

For absorbent structures having relatively high concentrations of these hydrogel-forming absorbent polymers, other characteristics of these absorbent polymers are also important. It has been found that the openness or porosity of the hydrogel layer formed when these absorbent polymers swell in the presence of body fluids is relevant for determining the ability of these absorbent polymers to acquire and transport fluids, especially when the absorbent polymer is present at high concentrations in the absorbent structure. Porosity refers to the fractional volume that is not occupied by solid material. For a hydrogel layer formed entirely from a hydrogel-forming absorbent polymer, porosity is the fractional volume of the layer that is not occupied by hydrogel. For an absorbent structure containing the hydrogel, as well as other components, porosity is the fractional volume (also referred to as void volume) that is not occupied by the hydrogel, or other solid components (e.g., fibers). A good example of a material having a very-high degree openness is an air-laid web of wood-pulp fibers.

An alternative/additional method to increase acquisition speed is to create void space or reservoir near the surface of the article: see U.S. Pat. Nos. 3,364,931; 4,029,101; and 4,501,586. However, the void space or the reservoir—taken per se—is not able to retain the liquid, making the articles incapable to provide dryness.

U.S. Pat. No. 5,827,254 discloses an absorbent article having a pair of spaced apart resilient region, an acquisition component and core. This article is able to rapidly accept and contain a large body fluid without leakage (gasketing effect).

In PCT Publication WO 01/21873 an absorbent composite is disclosed including one or more fibrous bands in a fibrous base. This arrangement acquires and distributes liquid on successive liquid insults (thus essentially avoiding gel blocking).

Canadian Patent Application 2,306,605 discloses an air-laid absorbent sheet with a functional embossing pattern that is operative to preferentially convey the body liquids along the sinuate compressed regions formed thereby.

OBJECTS AND SUMMARY OF THE INVENTION

Despite the extensive efforts documented by the prior art documents referred to in the foregoing, there is a continuous need to identify a structure able to provide at the same time i) absorption capacity, ii) leakage protection, and iii) dryness. Moreover, there is a growing need of absorbent articles that may combine protection with comfort and discreetness, while avoiding the disadvantages intrinsic to the prior art considered in the foregoing.

A basic object of the present invention is to provide thoroughly satisfactory responses to the needs outlined in the foregoing.

According to the present invention that object is achieved by means of a disposable absorbent product having the features set forth in the claims that follow, these claims being in all respects an integral part of the present disclosure. The invention also relates to a corresponding method of manufacture.

A preferred embodiment of the invention is a disposable absorbent product including a liquid pervious topsheet, a liquid impervious backsheet, and an absorbent core positioned between the topsheet and the backsheet. The absorbent core has a liquid receiving surface directed towards the topsheet and the absorbent core is provided with at least one embossing forming a channel for liquid drainage at the receiving surface, the channel having longitudinal sides. An acquisition layer is provided between the topsheet and the absorbent core, and a resilient absorbent member is provided having a region of higher liquid permeability in correspondence with the embossing. This region of higher liquid permeability can be produced e.g. by causing the resilient absorbent member to be thinner and/or have a discontinuity (e.g. one or more holes) in correspondence with the embossing. The discontinuity may also be created by providing the resilient absorbent member is in the form of stripes arranged longitudinally spaced along the longitudinal sides of the channel formed by the embossing. The discontinuity (i.e. the spacing) between the stripes defines the region of higher liquid permeability in correspondence with the embossing.

Preferably, the absorbent core contains a rather high amount of absorbent gelling material.

Still preferably the at least one embossing extends into the absorbent core for a substantial amount of the total thickness of the absorbent core.

In a particularly preferred embodiment the acquisition layer extends into the at least one embossing to form an internal lining thereof and/or over the upper faces of the absorbent members.

The resilient member is preferably located over the absorbent core, while the acquisition layer is preferably located right under the topsheet. The resilient member is preferably comprised of a material that maintains its shape when wet such as, e.g., fibrous cross-linked cellulosic fibers. The resilient member may contain absorbent gelling material.

BRIEF DESCRIPTION OF THE DRAWINGS

The invention will now be described, by way of example only, by referring to the enclosed figures of drawing, wherein:

FIG. 1 is a schematic general view of a disposable absorbent product as described herein;

FIG. 2 is a cross-sectional view along line II-II of FIG. 1; and

FIG. 3 is a corresponding cross-sectional view of a comparative reference product.

DETAILED DESCRIPTION OF PREFERRED EMBODIMENTS OF THE INVENTION

A preferred embodiment of a disposable absorbent product 20 of the present invention is shown in FIG. 1.

As shown in FIG. 1, the product 20 is in the form of e.g. a baby diaper or an adult incontinence pad. The product is shown in FIG. 1 in an extended condition, e.g. in preparation for being worn by a wearer.

It will be appreciated, however, that the same basic principles of the invention described herein are however adapted to be easily applied to other types of disposable absorbent products such as e.g., sanitary napkins.

In the case of a baby diaper or an adult incontinence pad the product 20 typically comprises an absorbent means (or "main body portion") 21, and four flaps 22 adding up to a general "hourglass" shape. The product 20 is thus adapted to be worn in a well known manner by placing the main body portion 21 under and around the "crotch" portion of the wearer. The flaps 22 are then extended and connected (via fasteners such as e.g. adhesive tabs 23) at their mutual opposed distal portions at both sides of the wearer to close the product around the waist line of the wearer.

The absorbent product 20 has two surfaces, a body-facing surface or "body surface" 20A and an outer surface 20B. The absorbent product 20 is shown in FIG. 1 as viewed from its body surface 20A. The body surface 20A is intended to be worn adjacent to the wearer's body.

The absorbent product 20 has two centerlines, a principal longitudinal centerline L and a principal transverse centerline T. The term "longitudinal", as used herein, refers to a line, axis or direction in the plane of the absorbent product 20 that is generally aligned with (e.g., approximately parallel to) a vertical plane which bisects a standing wearer into left and right body halves when the absorbent product 20 is worn. The terms "transverse" or "lateral" used herein, are interchangeable, and refer to a line, axis or direction which lies within the plane of the absorbent product 20 that is generally perpendicular to the longitudinal direction.

FIG. 1 shows that the main body portion 21 of the absorbent product 20 comprises the portion of the absorbent product without the flaps 23. The main body portion 21 has two spaced apart longitudinal edges, two spaced apart transverse or end edges (or "ends"), which together form the periphery of the main body portion 21. The main body portion 21 also has two end regions, which are designated first end region 21a and second end region 21b. A central region 21c is disposed between the end regions 21a and 21b.

The main body portion 21 of the absorbent product 20 can be of any thickness, including relatively thick, intermediate thickness, relatively thin, or even very thin (or "ultra thin"). The main body portion 21 of the absorbent product 20 may also be relatively flexible, so that it is comfortable for the wearer.

It should, however, be understood that the absorbent product shown is merely an example of embodiments, and that the present invention is not limited to absorbent articles of the type or having the specific configurations shown in the drawings.

FIG. 2 shows the individual components of the main body portion 21 of the absorbent product 20 of the present invention.

The main body portion 21 of the absorbent product preferably comprises a number of primary components. These include a liquid pervious topsheet 24, a liquid impervious backsheet 26, and an absorbent core 28 positioned between the topsheet 24 and the backsheet 26.

As will become evident from the following, the absorbent core 28 being indicated as "positioned" between the topsheet 24 and the backsheet 26 does in no way imply the necessity of direct contact between the absorbent core 28 and either of the topsheet 24 and the backsheet 26.

The absorbent core 28 has a liquid receiving surface directed towards the topsheet 24 (i.e. upwardly, with reference to FIG. 2). The absorbent core 28 may contain a large amount absorbent gelling materials.

In fact, the absorbent article shown herein has in the central region a high void volume thanks to a deep embossing 50, preferably extending into the absorbent core 28 to a large extent of the total thickness (i.e. the vertical dimension, with reference to the view of FIG. 2) the absorbent core 28.

Preferred embodiments of the arrangements described herein provide for the embossing 50 having a depth that is at least 30% of the total thickness of the absorbent core 28. Particularly preferred values are in the range 40%-95%, and still more preferred values lie in the ranges 50%-90% and 60%-80% of the total thickness of the absorbent core 28.

Preferred embodiments of the arrangements described herein provide for the embossing 50 having a length that is at least 3%, preferably at least 20%, more preferably at least 30% of the length of said absorbent core (28). A value of about 40% the core length is at present the absolutely preferred one.

When shorter than the core length, the embossing(s) 50 is/are preferably axially located with respect to the absorbent core 28 in correspondence of the so-called "deposition zone", i.e. the zone where bodily fluids are expected to be discharged.

Preferred embodiments of the arrangements described herein provide for the embossing 50 having a width that is at least 1 mm. Particularly preferred values are in the range 2-40 mm, and still more preferred values lie in the ranges 4-20 mm and 6-10 mm. A value of about 8 mm is at present the absolutely preferred one.

A resilient absorbent member is also provided that, in the exemplary embodiment shown, is comprised of two stripes 30 arranged longitudinally spaced along the upper the sides of the embossing 50. In alternative embodiments, the resilient member 30 or at least a part of the resilient member 30 extends down into the embossing 50.

An acquisition component 40 is preferably present and extends over the absorbent member(s) 30 and down into the embossing 50 to form an internal lining thereof.

The special combination of the channel or channels provided by the embossing 50 with the resilient absorbent member 30 and the preferably present acquisition component 40 was found to create and maintain a high void volume even under pressure and successive liquid insults.

Reference to "channel or channels" is intended to highlight that, while in certain embodiments the "composite" comprised of the core 28, the absorbent member 30, and the acquisition component 40 will include one channel, i.e. one embossing 50, in other embodiments, the composite will include two or more channels, i.e. one or more embossed formations 50.

The channel patterns may be of various kinds (e.g.: linear, curved, diamond-shaped, and so on). While longitudinal is preferred, the embossing pattern/acquisition-diffusion channel(s) 50 can have any orientation.

The resilient member 30 preferably comprises two stripes as shown in FIG. 2. The resilient member is preferably made of stripe members with a certain length, width and thickness and distance. Preferred ranges for the length, width and thickness of the stripes in the case of an absorbent article for adult incontinence use are 200-400 mm, 20-50 mm, and 2-10 mm, respectively. Still more preferably each stripe is about 300 mm long, and about 30 mm wide with a thickness of about 3-5 mm. In alternative embodiments, the resilient member 30 can be a single patch of any shape (for instance circular, rectangular, et.) with particular thickness and basis weight distribution e.g. lower or no thickness and basis weight in correspondence of the channel or channels, thus forming a region of higher liquid permeability in correspondence with such channel or channels.

In more general terms when considering also other types of absorbent articles constructed according to the present invention, such as for example baby diapers, it can be useful to refer to the size of the stripes in terms of percentages of the length of the core 28, rather than to their absolute size. In this more general case the stripes 30 typically have a length in the range of 80% to 20% of the core length, preferred ranges being 60% to 25% of the core length, and 50% to 30% of the core length.

Conversely, by referring to values in terms of percentages of the crotch width, i.e. the width of the product at the crotch portion, the stripes 30 typically have a width in the range of 45% to 5% of the narrower crotch width, a preferred range being 30% to 10% of narrower crotch width and a particularly preferred value being about 20% of the narrower crotch width.

Typically, the stripes 30 have a thickness in the range of 1 to 10 mm, preferred ranges being 2 to 7 mm and 3 to 5 mm.

While the resilient member 30 is preferably located onto the absorbent core 28 as shown in FIG. 2, it can be also located at different positions (e.g. above—and not under—the acquisition layer 40). The acquisition component 40 can thus be located at various positions (e.g. right under the topsheet 24, under the resilient member 30).

The acquisition component 40 may either be a separate component positioned e.g. between the topsheet 24 and the resilient member 30/absorbent core 28, or it may comprise part of a composite topsheet or part of the resilient member 30/absorbent core 28.

As further detailed in the following, the resilient member is preferably made of fibrous cross-linked cellulosic fibers, while the acquisition component 40 may be comprised of several different materials including nonwovens of synthetic fibers, natural fibers, and so on.

The basis weight of the acquisition component 40 is typically within the range of from about 20 g/sqm to about 200 g/sqm, preferably from about 30 g/sqm to about 120 g/sqm, and still more preferably from about 40 g/sqm to about 90 g/sqm. The thickness of the acquisition component 40 is preferably in the range of from about 0.2 mm to 8 mm, still more preferably in the range of from about 0.5 mm to 4.5 mm.

The absorbent core 28 preferably contains absorbent gelling material and cellulosic fibers. The percentage of absorbent gelling material is typically at least 20% and preferably higher than 30% of the total core weight. Particularly preferred ranges are 25%-95%; 30%-80%; 35%-70% by weight of absorbent gelling material over the total core weight.

The core 28 may also be free of (i.e. exempt from) cellulosic fibers.

The components of the absorbent product 20 may be comprised of any suitable materials that are capable of being bonded in the manner described herein.

The topsheet 24 is a liquid pervious component that permits liquids (e.g., urine and/or menses) to readily penetrate through its thickness. The topsheet 24 is preferably as compliant, soft feeling, and non-irritating to the wearer's skin as possible. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised at least partially of natural fibers (e.g., wood or cotton fibers), synthetic fibers (e.g., polymeric fibers such as polyester, polypropylene, or polyethylene fibers) or from a combination of natural and synthetic fibers.

In preferred embodiments of the present invention, the body surface of the topsheet 24 is hydrophilic so that liquids will be transferred through the topsheet more readily. This diminishes the likelihood that body fluids will flow off the topsheet rather than flowing into and being absorbed by the absorbent core. The body surface of the topsheet 24 can be made hydrophilic by treating it with a surfactant.

In the exemplary embodiment shown, the acquisition component (or "acquisition layer") 40 lies beneath the topsheet 24. The terms "layer" or "web", as used herein, include but are not limited to single unfolded sheets, folded sheets, strips of material, loose or bonded fibers, multiple layers or laminates of material, or other combinations of such materials. These two terms are thus, not limited to single unfolded layers or sheets of material.

The acquisition component 40 may provide void volume beneath the topsheet 24 to increase the ability of the absorbent product to draw liquids through the topsheet 24. In the preferred embodiment described herein, the acquisition component 40 preferably provides resiliency to lateral compressive forces so that the absorbent product 20 has improved resistance to bunching.

The acquisition component 40 may have an effective average pore size that is equal to that of the topsheet 24, or less than that of the topsheet 24.

The acquisition component 40 should be liquid permeable. The acquisition component 40 is also preferably compliant, soft feeling, and non-irritating to the user's skin. The acquisition component 40 has a body-facing face (or side), and may be of any suitable size and shape.

In the exemplary embodiment shown herein, the acquisition component 40 essentially mirrors the shape of the channel formed by the embossing 50 with the resilient member 30 arranged at the open mouth portion of the embossing 50. The dimensions of the acquisition component 40 are preferably not as large as those of the topsheet 24.

The acquisition component 40 can be made from any materials suitable for the above purposes, including, but not limited to those materials that are capable of having the topsheet 24 fused to them. The acquisition component 40 may, for example, be comprised of woven or nonwoven materials. The fibers or other components of these materials may be synthetic, or partially synthetic and partially natural. Suitable synthetic fibers include polyester, polypropylene, polyethylene, nylon, viscose rayon, or cellulose acetate fibers. Suitable natural fibers include cotton, cellulose, or other natural fibers. The acquisition component 40 may also be at least partially comprised of cross-linked cellulose fibers. The acquisition component 40, if nonwoven, can be made by a number of different processes. These include, but are not limited to: air laid, wet laid, meltblown, spunbonded, carded, thermally bonded, air-through bonded, powder bonded, latex bonded, solvent bonded, spunlaced, and combinations thereof. Suitable thermally bonded wet laid nonwoven webs are described in U.S. Pat. No. 5,549,589.

The acquisition component 40 may comprise a laminate of two materials. The two layers are preferably laminated together by depositing the multi-bonded air laid material on the spunbonded polypropylene nonwoven material. The spunbonded material is used as a process aid or carrier web in the process of forming this laminate.

In alternative embodiments, the spunbonded polypropylene nonwoven material may have a greater or a lower basis weight, or it may be replaced by an air laid tissue, a wet laid tissue, or any of the materials described above. If a wet laid tissue is used instead of a polypropylene nonwoven material, the orientation of the laminate is preferably reversed so that in the finished product, the multi-bonded air laid nonwoven material lies above the wet laid tissue layer. In the case of thicker absorbent products, any of the acquisition components described above can be used, Additionally, in one preferred thicker absorbent product embodiment, a low density latex bonded air laid material can be used as the entire acquisition component (that is, no tertiary topsheet is required).

However produced, the acquisition component 40 is preferably hydrophilic. The acquisition component 40 may be either less or more hydrophilic than the absorbent core 28, or it can have the same hydrophilicity as the absorbent core. If desired, the acquisition component 40 can be treated with a surface active agent to provide make it more hydrophilic. Preferably, it has the same hydrophilicity as the absorbent core.

As indicated, the topsheet 24 may be fused to the acquisition component 40. In that case, the topsheet 24 and the acquisition component 40 are preferably bonded at a plurality of discrete bonded areas (or "bonds"), continuous or discrete.

The discrete bonded areas preferably comprise fusion bonds. The fusion can be accomplished by heat and/or pressure bonds, ultrasonic bonds, dynamic mechanical bonds, and the like. Pressure can be applied in any suitable manner, such as by moving the components to be bonded between counter-rotating rolls, placing the material; on an anvil and forcing a platen down on the materials, applying vacuum pressure, and the like. Suitable means that can be adapted for use in fusing the topsheet 24 to the acquisition component 40 are described in at least some of the following patents: U.S. Pat. Nos. ,430,148; 4,515,595; 4,531,999; 4,710,189; 4,808,252; 4,823,783; 4,854,984; 4,919,756; and PCT Publication No. WO 93/11725.

The resilient member 30 is preferably made of material that maintains its shape even when wet, thus rendering the product 20 able to acquire sub sequential gushes.

To that effect, the resilient member 30 is preferably made of fibrous cross-linked cellulosic fibers. Alternatively, cross-linked natural rubber foam and synthetic rubber foam as well as numerous other types of resilient materials may be used for the resilient member 30. These include, but are not limited to, nonwoven highlofts, synthetic fiber batts, scrims (oriented, plastic netting which can be made with varying flexibility) and other forms of foam such as polyurethanes, such as those shown in U.S. Pat. Nos. 5,260,345; 5,268,224 and 5,331,015. In alternative embodiments, the resilient member 30 may contain absorbent gelling material.

The absorbent core 28 may be any absorbent means that is capable of absorbing or retaining liquids (e.g., urine and/or menses). The absorbent core 28 may be manufactured in a wide variety of sizes and shapes (e.g., rectangular, oval, hourglass, dog bone, asymmetric, etc.) depending on the type and nature of the disposable absorbent product considered. In the exemplary embodiment shown in the drawing, the absorbent core 28 is rectangular and is of a size that is at least slightly larger than the periphery of the acquisition component 40.

The absorbent core 28 can be manufactured from a wide variety of liquid-absorbent materials commonly used in absorbent products and other absorbent articles. Examples of suitable absorbent materials include comminuted wood pulp which is generally referred to as airfelt; creped cellulose wadding; meltdown polymers including coform; chemically stiffened, modified or cross-linked cellulosic fibers; synthetic fibers such as crimped polyester fibers; peat moss; tissue including tissue wraps and tissue laminates: absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradient, or lower density and lower average basis weight acquisition zones; or may comprise one or more layers or structures). The total absorbent capacity of the absorbent core should, however, be compatible with the design loading and the intended use of the absorbent product. Further, the size and absorbent capacity of the absorbent core may be varied to accommodate different uses such as incontinence pads, pantyliners, regular absorbent products, or overnight absorbent products.

The absorbent core 28 may comprise a multi-bonded air laid material. As an alternative to the absorbent core 28 being formed as a laminate, the fibers can be blended together to form a single web. In further alternative embodiments, the multi-bonded air laid material used for the absorbent core can be bonded using some material other than latex (such as starch or PVA, for example). In still further alternative embodiment, the absorbent core 28 can be formed as a laminate that preferably also has a basis weight of about 150 g/m and comprises two (or more) layers of multi-bonded air laid nonwoven material with the particles of absorbent gelling material therebetween.

Suitable laminate absorbent core structures are described generally in U.S. Pat. Nos. 4,950,264; 5,009,653; and 5,460,623. Another suitable absorbent core is described in PCT Publication No. WO 95/07674.

In the case of thicker absorbent products, the absorbent core 28 is preferably comprised of airfelt. Suitable absorbent cores for thicker absorbent products are described in U.S. Pat. No. 5,234,422.

In the above embodiments, or in other alternative embodiments, the absorbent core 28 can be provided with a feature to further improve its flexibility. Such a feature could include, but is not limited to one or more slits, perforations, embossments, or score lines in the absorbent core 28 or acquisition component 40. This type of feature is preferably arranged to improve flexibility about the principal longitudinal centerline of the absorbent product. The slits, perforations, embossments, or score lines can be in any suitable configuration. Suitable configurations include, but are not limited to straight or curved lines, slits, dots, V-shaped patterns, W-shaped patterns, or the like. The slits, perforations, embossments, or score line, or any combination thereof can be provided in any of the layers of the laminate absorbent cores described above.

The embossing 50 shown in FIG. 2, which runs along the principal longitudinal centerline L of the absorbent product, is exemplary of such a feature that will improve the flexibility of the absorbent core 28. However, in the arrangement disclosed herein, such embossing is of such an extent (i.e. depth and width) that together with the resilient member 30 and the acquisition component 40 the embossing 50 provides a high void space, thereby allowing rapid acquisition.

The embossing pattern 50 (possibly in the form of a plurality of channels) drains the liquid throughout the product reducing the transversal diffusion and the consequent side leakage. Moreover, it also reduces the risk of gel blocking by rapidly spreading the liquid on a wider area.

In the preferred embodiment as shown in FIG. 2, the embossing 50 involves the absorbent core 28 and the acquisition component 40 and preferably does not involve the topsheet 24. Arrangements wherein the embossing 50 also involves the topsheet 24 are however within the scope of the invention.

The backsheet 26 prevents the exudates absorbed and contained in the absorbent core 28 from undesirably exiting the product 20 thus possibly wetting articles which contact the absorbent product 20 such as pants, pijamas and undergarments.

The backsheet 26 is preferably resistant to the flow of liquids, and more preferably is impervious to liquids (e.g., urine and/or menses). The backsheet 26 is preferably manufactured from a flexible material. As used herein, the term "flexible" refers to materials which are compliant and will readily conform to the general shape and contours of the human body. The backsheet 26 may comprise a woven or nonwoven material, polymeric films such as thermoplastic films of polyethylene or polypropylene, or composite materials such as a film-coated nonwoven material, Preferably, the backsheet 26 is a polyethylene film having a thickness of from about 0.012 mm (0.5 mil) to about 0.051 mm (2.0 mils). The backsheet 26 may be embossed and/or matte finished to provide a more cloth like appearance. Further, the backsheet 26 may permit vapours to escape from the absorbent core 28 (i.e., breathable) while still preventing exudates from passing through the backsheet 26. A suitable backsheet material is obtained as product No. 18-1401 from the Clopay Corporation of Cincinnati, Ohio.

A suitable breathable backsheet material is a laminate of an apertured film such as that described in U.S. Pat. No. 3,929,135, which is inverted so that the smaller openings of the tapered capillaries face the absorbent core 42 which is adhesively laminated to a microporous film such as that described in U.S. Pat. No. 4,777,073.

The topsheet 24, the acquisition component 40, the resilient member 30, the absorbent core 28, and the backsheet 26 may be assembled in a variety of configurations known in the art (including layered or "sandwich" configurations and wrapped or "tube" configurations).

Preferably, the acquisition component 40 is joined to the absorbent core 28 within the embossing 50. If these components are joined, they can be joined in any of the manners described herein for joining the topsheet 24 to the acquisition component 40.

The topsheet 24 and the backsheet 26 have length and width dimensions generally larger than those of the absorbent core 21, and at the opposite ends of the product 20 the topsheet 24 and the backsheet 26 preferably extend outboard of the edges of the absorbent core 28 to form the flaps 22.

The portions of the topsheet 24 and backsheet 26 that extend beyond the edges of the absorbent core 28 (and the acquisition component 40) are preferably also joined to each other. These portions of the topsheet 24 and backsheet 26 can be joined in any suitable manner known in the art. The term "joined", as used in this specification, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown, these portions of the topsheet 24 and backsheet 26 are joined using adhesives over substantially the entire portions that extend beyond the edges of the absorbent core 28

Performance of a disposable absorbent product 20 as previously described was compared with an otherwise identical reference product having a cross section along line II-II as shown in FIG. 3.

Stated otherwise, the reference comprised a single resilient absorbent member (i.e. continuous patch 30R) and an absorbent core 28R exempt from any embossing.

While the reference product included also a topsheet 24 and a backsheet 26, no acquisition component 40 was provided in the reference product. The absorbent core 28R of the reference product contained absorbent gelling materials (about 20-25% of the core weight—i.e. more than about 25% of the core weight in the measured area).

The following tables provide a direct comparison of performance of the reference product ("reference") and the product described herein ("invention").

Specifically, the tests leading to the results reported below were performed on an adult incontinence product. The methods adopted for generating the comparison data reported in the tables can be summarized as follows.

I) Acquisition Speed is determined as the amount of liquid absorbed over a given time by the absorbent article under pressure.

The method adopted for determining the Acquisition Speed involves pre-conditioning (the absorbent articles shall be removed from packaging and unfolded and shall be conditioned for 2 hours at 23° C.±2° C. and 50% RH±5% RH) and uses the following test liquid formulation: 0.9% NaCl (as specified in ISO 6353-2) in demi-water (as specified in ISO 3696).

Procedure:
a) cut a rectangular sample (300×130 mm) from the central/crotch area of the absorbent article;
b) gently place a pressure template (300 mm×130 mm×9 mm with a "empty cylinder" in the center—515÷522 grams) and the associated weights (2×2,850 grams) on the sample;
c) start pouring a certain amount of test liquid (80 ml) on the center of the rectangular sample with a flow rate higher than 25 ml/sec;
d) simultaneously start the time count;
e) stop the time counting when the liquid disappears from the sample surface.

The ratio of the liquid volume absorbed to the time required to absorb it represents the acquisition speed of the absorbent member.

II) Rewetting is determined as the amount of liquid that is allowed to escape from the absorbent article under pressure.

Again, the absorbent articles are subject to pre-conditioning (the absorbent articles shall be removed from packaging and unfolded and shall be conditioned for 2 hours at 23° C.±2° C. and 50% RH±5% RH) and the test liquid has the formulation: 0.9% NaCl (as specified in ISO 6353-2) in demi-water (as specified in ISO 3696).

Procedure:
a) cut three contiguous square samples (105×105 mm) from the central/crotch area of the absorbent article;
b) pour a certain amount of test liquid (15 ml) on each square sample;
c) gently place a Plexiglas template (100×100×8 mm—90÷95 grams) and a weight (4500 grams) on the sample;
d) wait 10 minutes;
e) remove the template and the weight, apply a weighted stack of filter paper (200 g/sqm) on the samples and, again, gently place the template and the weight on the filter paper;
f) wait 2 minutes;
g) weigh the filter paper.

(Three samples are taken from each product to test performance over a wider area—the method provides reliable results even with one sample)

The gain in weight of the filter paper is recorded as Rewetting weight.

III) The Specific Absorbent Capacity is determined the amount of liquid absorbed by a weight unit of absorbent article.

Again, the absorbent articles are subject to pre-conditioning (the absorbent articles shall be removed from packaging and unfolded and shall be conditioned for 2 hours at 23° C.±2° C. and 50% RH±5% RH) and the test liquid has the formulation: 0.9% NaCl (as specified in ISO 6353-2) in demi-water (as specified in ISO 3696).

Procedure:
a) cut three contiguous square samples (100×100 mm) from the central/crotch area of the absorbent article;
b) weigh each square sample dry;
c) put the square sample in an inox wire sieve (Uni no. 32 mesh) and weigh;
d) sink the sieve in a reservoir containing the test fluid—the sample must be completely soaked;
e) wait 15 minutes;
f) lift the sieve, place it on a tray;
g) allow excess liquid to drain back under gravity from the samples in the sieve for two min;
h) apply a Plexiglas template (100×100×8 mm—90÷95 grams) and the weight (5,000 grams) on the sample;
i) wait 5 minutes;
l) weigh the sieve containing the sample wet.
(Again, three samples are taken from each product to test performance over a wider area—the method provides reliable results even with one sample)

The ratio between the gain in weight of the sample and the weight of the dry sample is recorded as Specific Absorbent Capacity.

IV) The Acquisition Speed—Multiple Insults parameter is determined as the time required by the absorbent article to absorb under pressure successive liquid insults. Pre-conditioning and test fluid are the same as for the Acquisition Speed.

Procedure:
a) follow the steps a) to e) of the Acquisition Speed method;
b) repeat three further times the steps c) to e) of the Acquisition Speed method waiting a fixed time between each repetition.

|  | Acquisition Speed ml/sec | Rewetting g | Specific Abs. Capacity g/g |
|---|---|---|---|
| Reference | 4.0 | 0.06 | 12.0 |
| Invention | 15.0 | 0.03 | 17.0 |

| Acquisition Speed—Multiple Insults | | | | |
|---|---|---|---|---|
| | | ml/sec | | |
| Reference | 1st gush | | | |
| | 2nd gush | | 4.0 | |
| | 3rd gush | 1.7 | 1.4 | 1.2 |
| | 4th gush | | 1.7 | |
| | Avg. | | | |
| Invention | 1st gush | | | |
| | 2nd gush | | 15.0 | 9.1 |
| | 3rd gush | | 6.8 | 5.7 |
| | 4th gush | | 8.0 | |
| | Avg. | | | |

The tests performed show that absorption capacity, leakage protection and dryness are all improved in the product described herein in comparison with the reference product.

The embossing pattern 50, the resilient member 30 and the optional preferred acquisition component 40 of the product described herein provide a high void space, this allowing rapid acquisition. The embossing pattern (channel) 50 drains the liquid throughout the product thus reducing the transversal diffusion and the consequent side leakage. It also reduces the risk of gel blocking by spreading rapidly the liquid on a wider area. The resilient members 30 create a gasketing effect. Since the resilient members are made of material that maintain their shape even when wet, they render the product able to acquire sub-sequential gushes. The acquisition component 40 provides a void space and separates the topsheet 24 from the absorbing core 28. The distance between the topsheet 24 and the core 28 allows also a better rewetting. The absorbent core 28 is rich in absorbent gelling material and thus offers high absorption capacity and dryness.

The arrangement described herein permits manufacturing a present invention leads to a main body portion 21 containing a smaller amount of cellulosic fibers, which is also comfortable. The possibility of using a high amount of absorption gelling material without the risk of inducing "gel blocking" leads to a a high absorption capacity with reduced bulkiness (a typical drawback of cores made of cellulosic fibers).

Moreover, the structure described herein (and specifically the embossing pattern 50 and the resilient members 30) improve the product fit to the wearer's body (easy bending in cross direction—vertical lift), while also improving the ability to capture the liquid closer to the source.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent product including a liquid pervious topsheet, a liquid impervious backsheet, an absorbent core positioned between the topsheet and the backsheet, and an acquisition layer positioned between the topsheet and the absorbent core, the absorbent core having a liquid receiving surface directed towards said topsheet, wherein:
   the absorbent core is provided with at least one embossing forming a channel for liquid drainage at said receiving surface, and
   a resilient absorbent member that maintains its shape when wet and consists essentially of fibrous cross-linked cellulosic fibers, nonwoven highlofts, synthetic fiber batts, and scrims or combinations thereof, is provided between the topsheet and the absorbent core, the resilient absorbent member having a region of higher liquid permeability in correspondence with said at least one embossing;
   wherein the acquisition layer extends into said at least one embossing to form an internal lining thereof, while said topsheet bridges said at least one embossing.

* * * * *